United States Patent
Maeda et al.

(10) Patent No.: US 9,452,264 B2
(45) Date of Patent: Sep. 27, 2016

(54) MOLD FOR GASKET FOR PREFILLED SYRINGE

(71) Applicant: SUMITOMO RUBBER INDUSTRIES, LTD., Kobe-shi, Hyogo (JP)

(72) Inventors: Katsushi Maeda, Kobe (JP); Junji Tashiro, Kobe (JP); Hiroaki Nakano, Kobe (JP); Eiji Yao, Kobe (JP)

(73) Assignee: SUMITOMO RUBBER INDUSTRIES, LTD., Kobe-Shi (JP)

( * ) Notice: Subject to any disclaimer, the term of this patent is extended or adjusted under 35 U.S.C. 154(b) by 0 days.

(21) Appl. No.: 14/244,602

(22) Filed: Apr. 3, 2014

(65) Prior Publication Data

US 2014/0228774 A1 Aug. 14, 2014

Related U.S. Application Data

(63) Continuation of application No. 13/598,720, filed on Aug. 30, 2012, now abandoned.

(30) Foreign Application Priority Data

Aug. 31, 2011 (JP) .................................. 2011-189522

(51) Int. Cl.
| | |
|---|---|
| *A61M 5/315* | (2006.01) |
| *B29C 33/42* | (2006.01) |
| *B29C 43/18* | (2006.01) |
| *B29C 33/38* | (2006.01) |
| *B29C 70/68* | (2006.01) |
| *B29L 31/00* | (2006.01) |

(52) U.S. Cl.
CPC ...... *A61M 5/31513* (2013.01); *B29C 33/3842* (2013.01); *B29C 33/42* (2013.01); *B29C 43/184* (2013.01); *B29C 70/68* (2013.01); *A61M 5/31511* (2013.01); *A61M 2207/10* (2013.01); *B29L 2031/7544* (2013.01)

(58) Field of Classification Search
CPC .............. B29C 37/0053; B29C 37/02; B29C 2059/027; B29C 2073/262
See application file for complete search history.

(56) References Cited

U.S. PATENT DOCUMENTS

| | | | |
|---|---|---|---|
| 3,656,731 A | 4/1972 | Larsen | |
| 4,143,489 A * | 3/1979 | Sogner | 451/135 |
| 5,756,243 A | 5/1998 | Matsuoka | |
| 6,090,081 A * | 7/2000 | Sudo et al. | 604/230 |
| 6,800,849 B2 * | 10/2004 | Staats | 250/288 |
| 6,807,838 B2 | 10/2004 | Iwaya | |
| 2002/0068108 A1 | 6/2002 | Iwaya | |
| 2004/0005436 A1 | 1/2004 | Mori et al. | |

(Continued)

FOREIGN PATENT DOCUMENTS

| | | |
|---|---|---|
| EP | 2055405 A1 | 5/2009 |
| JP | 11207751 A | 8/1999 |

(Continued)

*Primary Examiner* — Stella Yi
(74) *Attorney, Agent, or Firm* — Birch, Stewart, Kolasch & Birch, LLP

(57) ABSTRACT

A pre-filled syringe with excellent air-tightness and liquid-tightness and a mold for forming the gasket are provided. At least a surface of the mold for a gasket laminated with an inactive film for a pre-filled syringe forms a seal sliding surface of an annular protrusion of the gasket is mirror finished to have an arithmetic mean roughness Ra of less than 0.03 μm.

3 Claims, 1 Drawing Sheet

(56) References Cited

U.S. PATENT DOCUMENTS

| | | |
|---|---|---|
| 2004/0084852 A1 | 5/2004 | Tachikawa et al. |
| 2006/0035088 A1 | 2/2006 | Takano et al. |
| 2006/0035104 A1 | 2/2006 | Sugano et al. |
| 2006/0284345 A1 | 12/2006 | Sudo et al. |
| 2007/0245799 A1* | 10/2007 | Asakawa ............ B21J 13/02 72/467 |
| 2008/0093764 A1 | 4/2008 | Ito et al. |
| 2009/0177186 A1* | 7/2009 | Delano .................. 604/534 |
| 2009/0280208 A1 | 11/2009 | Sato et al. |
| 2010/0071434 A1 | 3/2010 | Tamai et al. |
| 2010/0308509 A1 | 12/2010 | David et al. |
| 2011/0247365 A1 | 10/2011 | Hayakawa et al. |
| 2012/0256349 A1 | 10/2012 | Ohara |

FOREIGN PATENT DOCUMENTS

| | | | |
|---|---|---|---|
| JP | 2001-246646 A | 9/2001 | |
| JP | 2002-86481 A * | 3/2002 | ............ B29C 43/18 |
| JP | 2002-86481 A | 3/2002 | |
| JP | 2002100523 A | 4/2002 | |
| JP | 2005-185747 A | 7/2005 | |
| JP | 2006-347098 A | 12/2006 | |
| JP | 2009061465 A | 3/2009 | |
| WO | WO 2010071050 A1 | 6/2010 | |

* cited by examiner

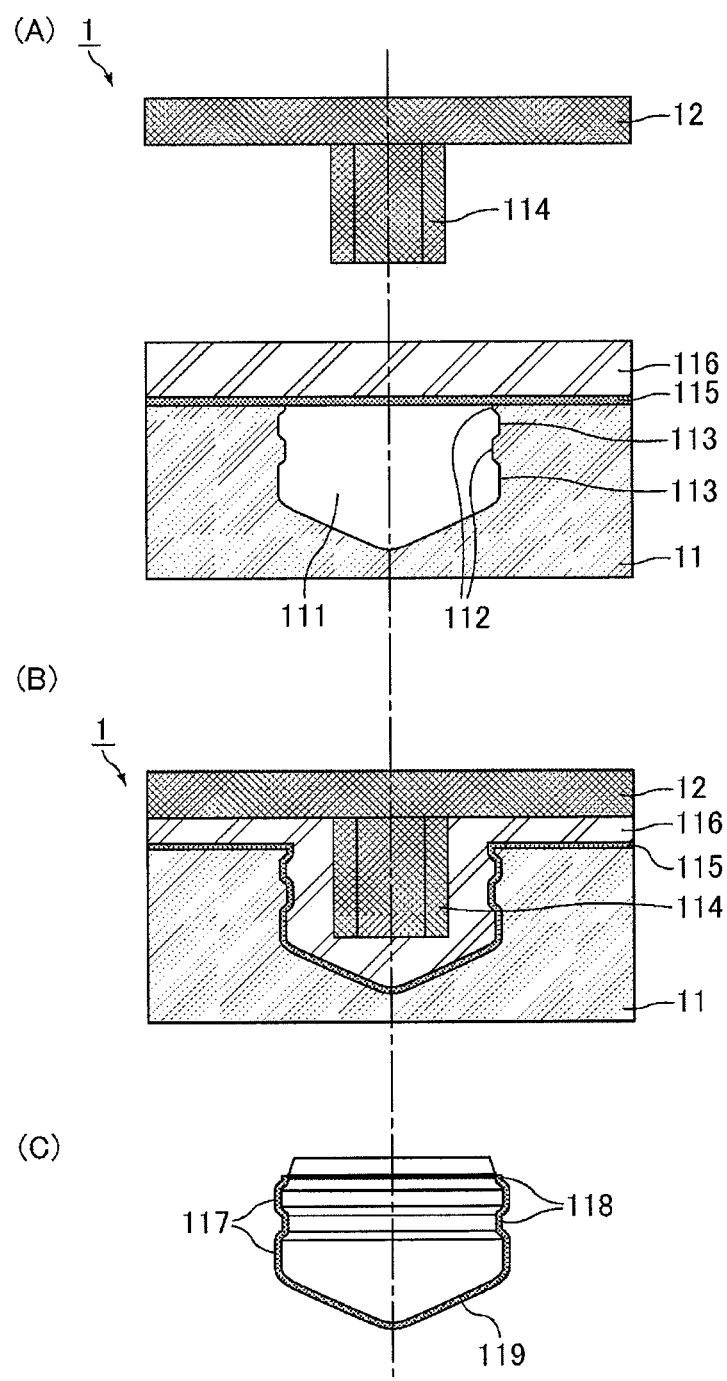

MOLD FOR GASKET FOR PREFILLED SYRINGE

CROSS-REFERENCE TO RELATED APPLICATION

This application is a Continuation of U.S. application Ser. No. 13/598,720, filed on Aug. 30, 2012, which claims priority under 35 U.S.C. §119(a) on Patent Application No. 2011-189522, filed in Japan on Aug. 31, 2011, the contents of each are hereby expressly incorporated into the present application.

TECHNICAL FIELD

The present invention relates to a mold for a gasket for a pre-filled syringe and a gasket for a pre-filled syringe produced using the mold.

BACKGROUND ART

Recently, the use of pre-filled syringes, which are syringes already filled with a drug, has become popular due to their good user-friendliness and in view of preventing medical accidents such as mix-up of drugs (Patent Document 1). The front end portion of a pre-filled syringe to which a needle is to be attached is sealed with a nozzle cap. Prior to injection, the nozzle cap is removed from the front end portion and a needle is attached thereto. A gasket is then slid by pushing a plunger rod toward the front end portion so that the drug is expelled.

For such pre-filled syringes, silicone lubricants are widely used. However, they cannot be used for those intended for biopharmaceuticals and the like because they cause inactivation of these drugs. Therefore, recently, in order to secure the stability of drugs, gaskets laminated with a fluororesin film have been widely used. Since the air-tightness and liquid-tightness of gaskets have an impact on the quality and stability of drugs, the gaskets are required to have high levels of these important properties. However, when used with a glass or resin syringe, gaskets laminated with a fluororesin film problematically exhibit poorer air-tightness and liquid-tightness than conventional, non-laminated rubber ones.

In particular, gaskets produced by laminate molding a skived PTFE film using a conventional mold allow liquid to leak out after sterilized by steam. Even in the case that such a gasket is designed to have an annular protrusion that provides a wider sealing width to improve its sealing performance, the air-tightness and the liquid-tightness are not improved. Moreover, in the approach to increase the annular rib diameter to increase compressibility, some problems may arise such as difficulty in setting the gasket in a syringe and creases on the stacked film around an annular sealing portion of the gasket. Still another problem is high resistance against sliding of a piston. Thus, such approach cannot provide an effective solution.

Patent Document 1: JP 2005-185747 A

SUMMARY OF THE INVENTION

An object of the present invention is to provide a gasket for a pre-filled syringe which overcomes the above problems and has excellent air-tightness and liquid-tightness, and a mold for forming the gasket.

The present invention relates to a mold for a gasket laminated with an inactive film for a pre-filled syringe, wherein at least a surface of the mold which forms a seal sliding surface of an annular protrusion of the gasket is mirror finished to have an arithmetic mean roughness Ra of less than 0.03 µm.

Regarding the mold for a gasket for a pre-filled syringe, the mirror finishing is preferably mirror polishing using an abrasive made of alumina or diamond.

The mold for a gasket for a pre-filled syringe is preferably made of a stainless steel mold material or a plated stainless steel mold material with a plating thickness of not more than 15 µm.

Regarding the mold for a gasket for a pre-filled syringe, the inactive film is preferably a 20 to 200 µm-thick film of polytetrafluoroethylene, ethylene tetrafluoroethylene copolymer, or ultra-high molecular weight polyethylene, formed by skiving, inflation, or extrusion.

The present invention also relates to a gasket laminated with an inactive film for a pre-filled syringe, which is produced by molding at 155° C. to 200° C. using the mold.

In the mold for a gasket laminated with an inactive film for a pre-filled syringe of the present invention, at least a surface of the mold which forms a seal sliding surface of an annular protrusion of the gasket is mirror finished to have an arithmetic mean roughness (Ra) of less than 0.03 µm. The use of this mold enables the production of a molded product including an inactive film that is laminated thereon and adjusted to have a small surface roughness. Thus, the present invention provides gaskets having excellent air-tightness and liquid-tightness.

BRIEF DESCRIPTION OF THE DRAWINGS

FIGS. 1A, 1B, and 1C are cross-sectional views schematically illustrating production processes of a gasket and an overall view of the obtained gasket.

MODES FOR CARRYING OUT THE INVENTION

In the mold for a gasket laminated with an inactive film for a pre-filled syringe of the present invention, at least a surface of the mold which forms a seal sliding surface of an annular protrusion of the gasket is mirror finished to have an arithmetic mean roughness (Ra) of less than 0.03 µm. Here, the arithmetic mean roughness (Ra) is determined using a cutoff value of 0.08 mm.

In the production of a gasket or nozzle cap which is laminated with an inactive film, even if a PTFE film having an arithmetic surface roughness Ra of not more than 0.05 µm, which has been conventionally recommended, is laminate molded at a temperature (e.g. 170° C.) lower than the melting point 330° C. of PTFE, fine irregular marks on the surface of a mold may be transferred on the surface of the stacked film, which may adversely affect the sealing performance of the product and problematically lead to liquid leakage. Here, a possible reason why fine marks due to cutting are formed on the mold is as follows. In a mold cutting process, asperities such as circular tool marks or an orange peel surface are formed on a partial surface area of the processed product due to vibrations between the equipment and tool and the mold and according to the sharpness of a cutting tool bit, the nature of the mold material, and the cutting conditions, which results in deterioration of surface roughness and therefore a loss of smoothness.

Generally, a polishing/buffing process is performed after the cutting process. Nonetheless, micro irregular tool marks remain on the surface of conventional molds. In the case that such a mold is used for forming a laminated rubber member, its rough surface adversely affects the sealing performance of the resulting rubber product even if the film to be laminated is smooth such as having an Ra of not more than 0.05 µm. On the contrary, the present invention makes it possible to produce a laminated gasket which has excellent sealing performance even if a skived film having an Ra of more than 0.05 µm is stacked because the mold has been mirror finished to adjust the Ra of the mold surface.

Hereinafter, the present invention is described in detail by way of embodiments but is not limited to only these embodiments.

FIGS. 1A to 1C are cross-sectional views schematically illustrating production processes of a laminated gasket using a mold 1 for a gasket for a pre-filled syringe of the present invention, and an overall view of the obtained gasket.

The mold 1 consists of a female mold member (lower member) 11 and a male mold member (upper member) 12, and the male mold member 12 is provided movably relative to the female mold member 11 in the up and down directions of FIG. 1. The female mold member 11 and the male mold member 12 can be heated by heaters (not shown) respectively connected to these members. Examples of heat sources of the heaters include electric heaters, steam, and oil.

The material of the mold 1 that consists of the female mold member 11 and the male mold member 12 is not particularly limited and may be a conventional material for molds. Preferred examples thereof include carbon steel and precipitation stainless steel. The mold 1 can be produced by a cutting method such as a method that includes a cutting process using a cemented carbide tool, a coated cemented carbide tool, a cBN sintered tool, or the like, and then polishing and mirror polishing processes.

The female mold member 11 is provided with a recess 111 extending inwardly from the periphery. The recess 111 is formed to correspond to the shape of a desired gasket.

The recess 111 of the female mold member 11 is provided with annular protrusion forming parts 113 which are formed to correspond to the shape of annular protrusions of the desired gasket. In each annular protrusion forming part 113, the surface of the mold which forms a seal sliding surface of the corresponding annular protrusion (sliding surface forming part) is mirror finished to have an arithmetic mean roughness Ra, as determined using a cutoff value of 0.08 mm, of less than 0.03 µm.

The recess 111 can be formed, for example, by a method that includes a cutting process for forming a cavity for a gasket using a cemented carbide forming tool, and an undercutting process for the annular protrusions. An alternative method is electrical discharge machining.

If the cutting process is performed by a high-speed cutting method in which a cutting blade of a cemented carbide tool, a coated cemented carbide tool, a cBN sintered tool, or the like mentioned above is rotated at a speed of higher than that in usual methods (e.g. higher than 100,000 rpm) for cutting, the depth of a notch made by the cutting blade can be reduced, resulting in a reduction in the man-hours required for mirror polishing which is performed after the cutting process.

Alternatively, an electroforming may be used. The electroforming is a method including polishing a part that is regarded as an undercut in a usual cutting process and thus cannot be seen by eyes. The electroforming is excellent in terms of working efficiency because the polishing is carried out in the production of a master for a cavity block, that is, the polishing is performed on its exposed protrusions corresponding to the sealing portions of a gasket to be produced, so that the polished state can be easily observed.

First, a master for a mold block corresponding to the product is prepared from a brass, aluminum alloy, or the like. The master is polished at this time. Next, hard chrome plating is applied to the master and a nickel-cobalt alloy is further added thereto. Then, cutting is performed on the added portion around the master to define the external dimension of the block. The master is removed by melting so that the cavity block is prepared.

Examples of polishing methods for mirror polishing the annular protrusion forming parts 113 without using an abrasive include polishing using a high-output ultrasonic polishing machine; electrolytic polishing for selectively melting fine projecting asperities on the surface of the mold; and chemical polishing in which asperities are molten with a processing solution to smooth the surface.

Suitable examples of the electrolytic polishing include various methods described in "aluminum handbook", 6th edition, published by Japan Aluminum Association, 2001, pp. 164-165; the method described in U.S. Pat. No. 2,708,655; and the method described in "Practical Surface Technology (Jitsumu Hyomen Gijutsu)", vol. 33, No. 3, 1986, pp. 32-38.

Suitable examples of the chemical polishing include various methods described in "aluminum handbook", 6th edition, published by Japan Aluminum Association, 2001, pp. 164-165. Other suitable examples thereof include a phosphoric-nitric acid method, Alupol I and V methods, an Alcoa R5 method, a $H_3PO_4$—$CH_3COOH$—Cu method, and a $H_3PO_4$—$HNO_3$—$CH_3COOH$ method.

Alternatively, examples of polishing methods involving the use of an abrasive include manual polishing and machine polishing, and an appropriate one is selected depending on the particular material of the mold and the quenched state. In these methods, mirror polishing is performed after wet or dry buffing. Mirror polishing or super mirror polishing to remove tool marks caused by cutting with a tool bit may be carried out by polishing the workpiece with a rotating buff or grindstone, or by hand.

As polishing tools, soft woods and buffs made of felt, synthetic fibers, acrylic fibers, or the like may be used, and abrasive grains are applied to these buffs. In the mirror polishing process, the polishing tool is sequentially changed from a harder one to a softer one as well as changing from a coarser paste to a finer paste.

Examples of abrasives used for polishing and mirror finishing the mold include abrasive grains of diamond, alumina, silicon carbide, cubic boron nitride, boron carbide, zirconium oxide, manganese oxide, colloidal silica or the like. Examples of alumina include corundum abrasives such as white fused alumina, brown fused alumina, alumina-zirconia, monocrystalline fused alumina, and sintered alumina. Preferred examples of abrasive grains include those having a particle size of #600 to #15000 (more preferably not smaller than #8000), and these grains may be used in the form of fine particles or a paste. Specifically, polishing is performed by preparing abrasive grain pastes containing abrasives made of diamond, alumina, silicon carbide, and the like with a vegetable oil; and applying these abrasive grains, while being sequentially changed from coarser particles to finer particles, to soft woods such as willow or balsa, or buffs.

An alternative method may be used in which a diamond burnishing tool is pressed against the surface of the mold having been subjected to the cutting process, in the same manner as in ordinary tool bit processing, as a result of which projecting asperities are smoothened without producing cutting chips to reduce the surface roughness so that the dimensional change in the diameter is suppressed to not more than 0.01 mm.

The mold may be plated in order to improve its stain resistance upon molding and reduce the number of washes of the mold. The plating thickness is preferably not more than 15 µm, and more preferably not more than 10 µm. A thickness of more than 15 µm may cause a problem of the dimension accuracy of the annular protrusion diameter, the valley diameter, and the thread diameter.

As a result of mirror finishing of the sliding surface forming part, the part of the mold has a smooth surface having an arithmetic mean roughness Ra, as determined using a cutoff value of 0.08 mm, of less than 0.03 µm. The Ra is preferably not more than 0.02 µm, and more preferably not more than 0.015 µm. In the present invention, at least the sliding surface forming part is mirror finished to adjust the Ra to not more than a particular value, and the Ra of other surface parts in the recess 111 may also be adjusted. Further, the entire surface of the mold may be mirror finished to adjust the Ra. Preferably, the entire side face of the sliding portion forming part is mirror finished. This is because the surface of the annular protrusion may be likely to be damaged when the product is released from the mold after molding since the product is forcibly released through the valley of the cavity which has a narrower diameter.

In the present invention, the arithmetic mean roughness (Ra) is measured in accordance with JIS B0601-2001.

On the other hand, the male mold member 12 has an undersurface provided with a projection 114 for forming a fitting hole of the gasket. Although not shown in the figures, the projection is threaded to allow fitting of a plunger rod.

In the molding process, the mold 1 is preheated before molding a gasket. The preheat temperature is preferably 155° C. to 200° C.

Next, an inactive film 115 on which a mixture sheet 116 (unvulcanized rubber sheet) prepared from a material for a gasket body is stacked is placed on the upper surface of the female mold member 11. In this case, the male mold member (core) may be located below the female mold member (cavity) and then the unvulcanized rubber sheet on which the film is stacked may be placed on the male mold member (core).

The resin material for the inactive film 115 is not particularly limited but is preferably an olefin resin and/or at least one fluororesin selected from the group consisting of tetrafluoroethylene-ethylene copolymers (ETFE), polytetrafluoroethylene (PTFE), and polychlorotetrafluoroethylene (PCTFE) because they provide good chemical resistance. PTFE is, however, less resistant to gamma-ray radiation although medical containers are sterilized by steam, gaseous ethylene oxide, or gamma-ray radiation. Therefore, ETFE, modified ETFE, and PCTFE, which are highly resistant to gamma-ray radiation, are particularly preferred.

Here, "ETFE" means a copolymer of ethylene and tetrafluoroethylene at a molar ratio of 30/70 to 70/30, and "modified ETFT" means a copolymer of these components and other component(s) for modification. Examples of other components include fluoroolefins and hydrocarbon olefins. Specific examples thereof include α-olefins such as propylene and butene; fluoroolefins such as hexafluoropropylene, vinylidene fluoride, perfluorobutyl ethylene, and trifluorochloroethylene; vinyl ethers such as ethylene vinyl ether, perfluoromethyl vinyl ether, and perfluoropropyl vinyl ether; and fluoroacrylates. These are used as comonomers at a ratio of 2 to 10 mol % to modify ETFE.

Suitable examples of modified ETFE include ETFE having a functional group that imparts adhesiveness. Examples of such functional groups include a carboxyl group, an anhydrous carboxyl group, an epoxy group, a hydroxyl group, an isocyanate group, an ester group, an amide group, an aldehyde group, an amino group, a cyano group, a carbon-carbon double bond, a sulfonic acid group, and an ether group. Examples of commercial products of such modified ETFE include Fluon AH-2000 and AFLEX from Asahi Glass Co., Ltd.

Examples of olefin resins include polyethylene resins such as polyethylene, ethylene-propylene copolymers, ethylene-propylene-nonconjugated diene copolymers, ethylene-butene copolymers, ethylene-hexene copolymers, ethylene-octene copolymers, ethylene-vinyl acetate copolymers, ethylene-vinyl alcohol copolymers, ethyleneethyl acrylate copolymers, and chlorinated polyethylene; polypropylene resins such as polypropylene, propyleneethylene random copolymers, propylene-ethylene block copolymers, and chlorinated polypropylene; polybutene; polyisobutylene; polymethylpenten; and copolymers of cyclic olefins. Among these, polyethylene (in particular, ultra-high molecular weight polyethylene (UHMWPE)) is preferred. The olefin resins may contain fluorine.

The thickness of the inactive film 115 can be appropriately determined based on the shape and size of the desired gasket and is preferably 50 to 200 μm.

Since the surface roughness of the mold is less than 0.03 μm, the resulting laminated gasket has excellent liquid-tightness and air-tightness even if the inactive film 115 is an inflated film, a cast film or an extruded film having an arithmetic mean roughness Ra of 0.01 to 0.03 μm, or a skived film having an arithmetic mean roughness Ra of 0.10 μm. The lower limit of the Ra of the inactive film is not particularly limited.

The inactive film 115 is preferably subjected to a treatment for enhancing the adhesiveness to rubber or the like. Examples of the treatment for enhancing the adhesiveness include a chemical treatment, a treatment for roughening the film surface, and a combination of these, and specific examples thereof include a sodium treatment, a glow discharge treatment, a plasma treatment (electric discharge treatment) at atmospheric pressure or in vacuum, an excimer laser treatment (electric discharge treatment), and an ion beam treatment.

The mixture sheet 116 for forming a gasket body (gasket core) is made of an elastic material.

The elastic material for the gasket body is not particularly limited and examples thereof include various rubber materials such as natural rubber, butyl rubber, isoprene rubber, butadiene rubber, styrene-butadiene rubber, silicone rubber, epichlorohydrin rubber, ethylene propylene rubber, and nitrile rubber; and various thermoplastic elastomers such as polyurethane elastomers, polyester elastomers, polyamide elastomers, olefin elastomers, and styrene elastomers. Any of these elastic materials may be used alone, or two or more of these may be blended. Among these, materials that will be elastic through vulcanization are preferred. In the case of using such a material to be vulcanized, additives known in the rubber industry such as vulcanizing agents (e.g. sulfur) and vulcanization accelerators may be optionally added.

The mixture sheet 116 is prepared by mixing predetermined proportions of materials with a kneader such as an internal mixer or an open roll mill, and forming the resulting mixture into an unvulcanized rubber sheet by a calendar or a sheet forming machine. Subsequently, a piece of the unvulcanized rubber sheet which has a predetermined weight and size is stacked on the inactive film, and is then placed on the mold and formed by vacuum press molding into a molded sheet for a laminated gasket.

The molding conditions are not particularly limited and may be appropriately determined. The molding temperature is preferably 155° C. to 200° C., and more preferably 165° C. to 180° C., and the molding time is preferably 1 to 20 minutes, more preferably 3 to 15 minutes, and still more preferably 5 to 10 minutes.

Then, unnecessary portions of the molded product for a gasket are cut out and removed, and the resulting product is washed, sterilized, dried, and examined by an appearance test. In this manner, a complete gasket product is obtained.

The gasket laminated with an inactive film for a prefilled syringe as produced as above has a substantially cylindrical body, and the cylindrical side face and the liquid contact portion (head) of the gasket are covered with the inactive film 115. Ring projections (annular protrusions) projecting toward the inner periphery of a syringe barrel are formed on the cylindrical side face and spaced a predetermined distance from each other along the longitudinal direction. The projections (annular sealing portions) are compressed against and are closely in contact with the inner wall of the syringe when the gasket is slid. The number of annular protrusions is not particularly limited. The liquid contact portion is a portion which contacts a drug in the syringe but does not contact the inner wall of the syringe. Further, the gasket is provided with a threaded portion into which a plunger rod is fitted.

EXAMPLES

The following is set forth to specifically illustrate the present invention by way of examples but the present invention is not limited to only these examples.

The fluororesin films used in examples are listed below.

Homo-PTFE (polytetrafluoroethylene) skived film: VALFLON from Nippon Valqua Industries, Ltd.

Modified PTFE (tetrafluoroethylene-perfluoroalkoxide monomer copolymer) skived film: New VALFLON from Nippon Valqua Industries, Ltd.

Homo PTFE (polytetrafluoroethylene) cast film: cast film from GSI Creos Corp.

ETFE (ethylene-tetrafluoroethylene copolymer) extruded film: AFLEX from Asahi Glass Co., Ltd.

Modified ETFE (ETFE-another monomer copolymer) extruded film: AFLEX from Asahi Glass Co., Ltd.

(Surface Roughness Measurement)

The surface roughness was measured for the films as mentioned below.

Measuring method: based on JIS B0601-2001

Measuring instrument: laser microscope VK-9710 from KEYENCE Corp., lens magnification ×50

An about 5-cm square sample was cut out from each film and the surface of the sample which is opposite to the treatment surface to be adhered to rubber by vulcanization was measured to evaluate the surface roughness of each film.

Table 1 shows the details of the inactive films used in Examples and Comparative Examples.

Measuring method: based on JIS B0601-2001

Measuring instrument: laser microscope VK-9710 from KEYENCE Corp., lens magnification ×50

The surface roughness of the molds and the laminated rubber members was evaluated by measuring their portions corresponding to the annular protrusions and valleys using a laser microscope. As the cutting and polishing processes were performed along the circumferential direction of the molds, cutting marks would be formed in the circumferential direction. Hence, the surface roughness was measured along the direction vertical to the circumferential direction. In laser measurement for the surface roughness of the mold parts for forming the annular protrusions (sealing portions) and the valleys, the cavity blocks were cut by wire electric discharge and then measured regardless the size of gaskets. In the case of contact measurement, if the diameter of the annular protrusions to be measured of a gasket is not less than 13 mm, the cavity block can be measured as it is; if the diameter is less than 13 mm, the cavity block can be measured after being cut by wire electric discharge.

(Pressure Test)

Into syringe barrels from which water was sufficiently wiped away, water (colored indigo blue) was drawn to graduation lines corresponding to ¾ and ½ of the nominal capacity. Each barrel was horizontally fixed so as not to allow water to spill out from the nozzle, and a pressure of 343 kPa (3.5 Kgf) was then applied to the nozzle for 10 seconds. Each syringe was evaluated by determining whether water drops leaked out of the fitting part. The evaluation results are shown as "the number of syringes with leakage/the number of tested syringes".

TABLE 1

| Film | Kind | Homo PTFE | Modified PTFE | Homo PTFE | Modified ETFE |
|---|---|---|---|---|---|
| | Production method | Skiving | Skiving | Casting | Extrusion |
| | Thickness (μm) | 100 | 100 | 100 | 100 |
| Measurement condition | Instrument | Laser microscope | Laser microscope | Laser microscope | Laser microscope |
| | Number n of samples | 8 | 8 | 8 | 8 |
| | Cutoff value (mm) | 0.25 | 0.25 | 0.08 | 0.08 |
| | Evaluation length (mm) | 0.25 | 0.25 | 0.25 | 0.25 |
| Surface roughness Ra (μm) | | 0.08-0.14 | 0.09-0.12 | 0.02-0.03 | 0.01-0.02 |

Examples and Comparative Examples

Molds were designed to allow two annular protrusions of the gasket which correspond to sealing portions to have a compression ratio of 3.0% based on a syringe inner diameter (barrel diameter) of 12.45 mm.

An unvulcanized rubber sheet that contained chlorinated butyl rubber (JIS-A hardness: 58) was stacked on a 100 μm-thick inactive film and placed on a mold. They were adhered to each other through vulcanization by vacuum pressing for 10 minutes at 175° C. In this manner, gaskets laminated with an inactive film were formed as molded sheets. Curable silicone was applied by spray coating to one surface (thread side) of each molded sheet except the liquid contact surface and the sliding surfaces which were laminated surfaces. In the case of the modified ETFE film, the entire surface was spray coated with the curable silicone. Burrs were cut out (cut portion: 1.0 mm), and washing, sterilization, and drying were performed. In this manner, laminated gaskets were completed.

Prefilled syringes (nominal capacity: 5 ml, syringe inner diameter: 12.45 mm) were prepared using the obtained gaskets and evaluated by the following tests.

(Surface Roughness Measurement)

The surface roughness of the molds and the laminated rubber members (molded products) were measured as mentioned below.

(Suction Test)

Water was drawn into syringe barrels to a graduation line corresponding to ¼ of the nominal capacity, and the nozzle of each barrel was sealed. Each syringe was evaluated by determining whether bubbles continuously generated from the fitting part when a plunger was withdrawn to a graduation line corresponding to the nominal capacity. The evaluation results are shown as "the number of syringes in which continuous bubbles generated/the number of tested syringes".

(Gasket/Leakage after Steam Sterilization)

Prefilled syringes filled with 5 ml of water were sterilized at 125° C. for 30 minutes. After cooled, each syringe was evaluated by eyes by determining whether there was a leak to the valley (recess) between the annular protrusions of the gasket. The evaluation results are shown as "the number of syringes with leakage to the valley (recess)/the number of tested syringes".

Table 2 shows the evaluation results. The details of the inactive films used are also shown in Table 2. The entire surface of each mold was mirror finished and the Ras are those corresponding to the annular protrusions and the valleys.

TABLE 2

| Example No. | | Mold | | Film | | Laminated gasket (molded product) | Air-tightness test | | |
|---|---|---|---|---|---|---|---|---|---|
| | | Surface finish | Surface roughness Ra (μm) | Kind | Production method | Surface roughness Ra (μm) | Surface roughness Ra (μm) | Pressure test | Suction test | Leakage test after steam sterilization |
| Example | 1 | Mirror polishing | 0.01-0.02 | Homo PTFE | Skiving | 0.08-0.14 | 0.02-0.07 | 0/10 | 0/10 | 0/10 |
| | 2 | Mirror polishing | 0.01-0.02 | Homo PTFE | Casting | 0.02-0.03 | 0.02-0.03 | 0/10 | 0/10 | 0/10 |
| | 3 | Mirror polishing | 0.01-0.02 | Modified PTFE | Skiving | 0.09-0.12 | 0.02-0.07 | 0/10 | 0/10 | 0/10 |
| | 4 | Mirror polishing | 0.01-0.02 | Modified ETFE | Extrusion | 0.01-0.02 | 0.01-0.02 | 0/10 | 0/10 | 0/10 |
| | 5 | Electroforming | 0.01 | Modified PTFE | Skiving | 0.09-0.12 | 0.02-0.05 | 0/10 | 0/10 | 0/10 |
| Comparative Example | 1 | Shot peening | 0.23-0.37 | Modified PTFE | Skiving | 0.09-0.12 | 0.21-0.35 | 0/10 | 9/10 | 7/10 |
| | 2 | Cutting process only | 0.03-0.10 | Homo PTFE | Skiving | 0.08-0.14 | 0.04-0.11 | 0/10 | 2/10 | 4/10 |
| | 3 | Cutting process only | 0.03-0.10 | Modified PTFE | Skiving | 0.09-0.12 | 0.06-0.13 | 0/10 | 3/10 | 2/10 |
| | 4 | Cutting process only | 0.03-0.10 | Modified ETFE | Extrusion | 0.01-0.02 | 0.02-0.10 | 0/10 | 1/10 | 2/10 |

In Examples in which the Ra of the mold surface was adjusted to not more than a predetermined value, no leakage was observed, which demonstrates excellent liquid-tightness and air-tightness. On the contrary, in Comparative Examples in which the Ra of the mold surface was not adjusted to not more than the predetermined value, leakage was observed, which demonstrates poor liquid-tightness and air-tightness.

EXPLANATION OF SYMBOLS

1 Mold
11 Female mold member
12 Male mold member
111 Recess
112 Valley forming part
113 Annular protrusion forming part
114 Projection
115 Inactive film
116 Mixture sheet (unvulcanized rubber sheet)
117 Annular protrusion (projection)
118 Valley (recess)
119 Laminated portion

The invention claimed is:

1. A process for preparing a gasket laminated with an inactive film for a pre-filled syringe, the process comprising the step of:

molding a laminated sheet of an inactive film and an unvulcanized rubber sheet at 155° C. to 200° C. using a mold, wherein:

at least a surface of the mold which forms a seal sliding surface of an annular protrusion of the gasket is mirror finished to have an arithmetic mean roughness Ra of less than 0.03 μm, the mold is made of a stainless steel mold material or a plated stainless steel mold material with a plating thickness of not more than 15 μm, and the mirror finishing is performed along a circumferential direction of the mold.

2. The process for preparing a gasket for a pre-filled syringe according to claim 1, wherein the mirror finishing is mirror polishing using an abrasive made of alumina or diamond.

3. The process for preparing a gasket for a pre-filled syringe according to claim 1, wherein the inactive film is a 20 to 200 μm-thick film of polytetrafluoroethylene, ethylene tetrafluoroethylene copolymer, or ultra-high molecular weight polyethylene, formed by skiving, inflation, or extrusion.

* * * * *